United States Patent [19]

Dai

[11] Patent Number: 4,618,727
[45] Date of Patent: Oct. 21, 1986

[54] NITRO SUBSTITUTED DIPHENYL ETHERS

[75] Inventor: Shenghong A. Dai, Wallingford, Conn.

[73] Assignee: The Dow Chemical Company, Midland, Mich.

[21] Appl. No.: 668,540

[22] Filed: Nov. 5, 1984

[51] Int. Cl.$^4$ ............................................. C07C 79/35
[52] U.S. Cl. ................................... 568/585; 568/586; 564/315; 528/288
[58] Field of Search ................................ 568/585, 586

[56] References Cited

U.S. PATENT DOCUMENTS 4,339,612 7/1982 Kranz et al. ..................... 568/586 X
4,482,736 11/1984 Forster et al. .................. 568/586 X

OTHER PUBLICATIONS

Imai et al, J. Polymer Science, 1981, 19, pp. 3285-3291.

Primary Examiner—Bernard Helfin
Attorney, Agent, or Firm—J. S. Rose

[57] ABSTRACT

Nitro-isopropenyldiphenyl ethers are provided which can serve as a useful source of known monomer intermediates or as intermediates for the preparation of nitro-haloisopropyl substituted diphenyl ethers. The latter have been discovered to act as facile alkylating agents with phenols providing nitro-p-hydroxyphenylisopropyl substituted diphenyl ethers. When the latter compounds are reduced there are obtained the corresponding amino-p-hydroxyphenylisopropyl substituted diphenyl ethers.

The polymerization of this last class of compounds with acid halides provides polyamide-esters. The polymers can be used in the manufacture of such articles as tubing, hose, bellows hose, and the like.

12 Claims, No Drawings

NITRO SUBSTITUTED DIPHENYL ETHERS

FIELD OF THE INVENTION

This invention relates to the preparation of diphenyl ethers, and, more particularly, is concerned with the preparation of certain nitro substituted diphenyl ethers, and amino substituted diphenyl ethers and polyester-amide polymers derived from the latter ethers.

DESCRIPTION OF THE PRIOR ART

Diphenyl ethers having hydroxyl or amino groups substituted in each aromatic ring are known to be very useful monomers for the preparation of various polymer types including polyesters, polycarbonates, polyamides, polyamide-esters, and the like. Recently, diphenyl ethers having a hydroxyl on one aromatic ring and an amino group on the other have been used to prepare polyamide-esters; see Imai et al, J. Polymer Science, 1981, 19, pp. 3285-91.

Heretofore, the amino-hydroxyl substituted diphenyl ethers have been prepared via the Ullmann type reaction of hydroquinone or resorcinol with the appropriate halo-substituted nitrobenzene and subsequent reduction of nitro to amine. A serious drawback to the above procedure is the side-product formation of diether derivatives which leads to lowered yields of desired product and difficult separation and purification procedures.

I have now discovered a class of nitro-isopropenyl substituted diphenyl ethers which serve as intermediates for the preparation of known amino-hydroxyl aromatic ethers without the prior art problems of diether formation and the purification difficulties discussed above.

Further, the nitro-isopropenyl diphenyl ethers can be used to prepare a new class of nitro-haloisopropyl substituted diphenyl ethers. These latter ethers, it has been found, condense with phenols in a facile reaction to form intermediate nitro-hydroxyphenylisopropyl substituted diphenyl ethers which upon reduction form the corresponding amino-hydroxy derivatives.

The latter amino-hydroxy derivatives are used as monomers in the preparation of what is believed to be a novel class of polyamide-esters.

SUMMARY OF THE INVENTION

This invention comprises nitro substituted diphenyl ethers having the formula (I) wherein Q is

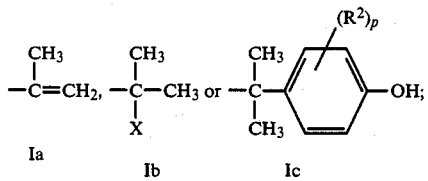

wherein R, $R^1$, and $R^2$ are independently selected from the group consisting of alkyl, aryl, aralkyl, and cycloalkyl; X represents halogen; and n, m, and p each have an independent value of 0 to 4, inclusive.

This invention also comprises a process for the preparation of said nitro substituted diphenyl ethers (Ic) which comprises heating said nitro substituted diphenyl ethers (Ib) with phenols having the formula (II) wherein $R^2$ and p are defined as above in (I) and provided the para position relative to the hydroxyl group in said phenol is free of any $R^2$ substituent groups.

This invention also comprises amino substituted diphenyl ethers having the formula (III) wherein R, $R^1$, $R^2$, n, m, and p are as defined above.

This invention also comprises polyamide-ester polymers having recurring units selected from the group consisting of formula IV, V, and mixtures thereof wherein R, $R^1$, $R^2$, n, m, and p are defined as above, and D is selected from the group consisting of alkylene, arylene, and cycloalkylene.

The term "alkyl" means lower-alkyl having from 1 to 8 carbon atoms, inclusive, such as methyl, ethyl, propyl, butyl, pentyl, hexyl, heptyl, octyl, and isomeric forms thereof.

The term "aryl" means the radical obtained by removing one nuclear hydrogen atom from an aromatic hydrocarbon having from 6 to 12 carbon atoms, inclusive, such as phenyl, tolyl, biphenylyl, and the like.

The term "aralkyl" means the monovalent radical obtained by removing one hydrogen atom from the alkyl portion of an aromatic alkane hydrocarbon having 7 to 18 carbon atoms, inclusive, such as benzyl, phenylethyl, phenylpropyl, benzhydryl, and the like.

The term "cycloalkyl" means cycloalkyl having 4 to 6 ring carbon atoms, inclusive, such as cyclobutyl, cyclopentyl, cyclohexyl, 3-methylcyclopentyl, 4-methylcyclohexyl, and the like.

The term "halogen" means fluorine, chlorine, bromine, and iodine.

The term "alkylene" means alkylene having 2 to 12 carbon atoms such as ethylene, propylene, butylene, pentylene, hexylene, heptylene, octylene, nonylene, decylene, undecylene, dodecylene, and isomeric forms thereof.

The term "arylene" means a divalent radical derived from an aromatic hydrocarbon having 6 to 12 carbon atoms, inclusive, such as phenylene, tolylene, xylylene, naphthylene, diphenylylene, and the like.

The term "cycloalkylene" means cycloalkylene having 4 to 6 ring carbon atoms, such as 1,3-cyclobutylene, 1,3-cyclopentylene, 1,4-cyclohexylene, 1,3-cyclohexylene, and the like.

DETAILED DESCRIPTION OF THE INVENTION

The diphenyl ethers (I) and (III) in accordance with the present invention can be prepared, and, are related, according to the generalized reaction scheme shown in the Reaction Chart.

The appropriately substituted isopropenyl phenol compound (VI) is readily condensed with the nitro-halo substituted benzene (VII) under basic conditions using procedures analogous to those known in the art for the formation of aromatic ethers to produce the ethers having the formula (Ia); R, $R^1$, X, n, and m in (VI) and (VII) have the same significance set forth above. Typical of such reaction procedures is the Ullmann aromatic ether synthesis (Ullmann et al., Annalen 350, 83, 1906).

A preferred prior art procedure for their preparation is the one disclosed by Sugano et al., Japanese Pat. No. 67,23,340 (Chem. Abstracts 69, 1968, 35718s) wherein the phenol and halobenzene starting materials are heated together at about 130° C. to about 175° C. in substantially equimolar proportions in an inert organic solvent and in the presence of a basic catalyst.

The term "inert organic solvent" means an organic solvent which does not enter into reaction with any of the reactants involved in the process or interfere in any other manner with the desired course of the reaction. Illustrative of inert organic solvents therefor are benzene, toluene, xylene, glyme (dimethylether of ethylene glycol), diglyme (dimethylether of diethylene glycol), triglyme (dimethylether of triethylene glycol); the dipolar aprotic solvents such as acetonitrile, dimethylformamide, diethylformamide, dimethylacetamide, dimethylsulfoxide, tetramethylsulfone, tetramethylurea, and the like.

A hydrohalic acid (HX) is produced by the reaction hence the need for a basic reagent. Generally speaking, the base is employed in sufficient amount to neutralize the acid formed, for example, at least in stoichiometric amount, preferably in excess over the mole proportions of (VI) and (VII). Any basic reagent capable of neutralizing the HX without interfering in the process can be employed. Illustrative, but not limiting, are organic bases such as triethylamine, tributylamine, and the like; and inorganic bases including the alkali metal and alkaline earth metal carbonates such as sodium and potassium carbonate, magnesium and calcium carbonate, and the like.

The starting isopropenylphenols are, for the most part, known compounds prepared by prior art procedures. Generally speaking, they are prepared by the alkaline pyrolysis or cracking by distillation of the appropriately substituted bisphenol A compound. Bisphenol A is 2,2-bis-(p-hydroxyphenyl)propane and is readily cracked into p-isopropenylphenol and phenol. For preparative procedures see, for example, U.S. Pat. Nos. 4,334,106 and 4,207,265 whose disclosures relative thereto are incorporated herein by reference. When isopropenylphenols are required having the formula wherein R groups are substituted on the aromatic ring in accordance with (VI) above, the appropriately substituted bisphenol A compounds are employed in the cracking process.

The nitro-halo substituted benzenes are for the most part commercially available and those which are not are easily obtained by known preparative methods. The meaning of X is the same as defined above, that is to say it can be chlorine, bromine, iodine, and fluorine, although, generally speaking, chloro- and bromobenzene derivatives are preferred for the reaction with (VI). While the nitro group can be substituted anywhere on the aromatic ring relative to the halogen group, it is preferred to be in either ortho- or para- relationship thereto to facilitate the condensation. Most preferably, the nitro is para to the halogen group.

Generally speaking, the reactants are heated together at a temperature falling within the ranges set forth above. The progress of the reaction can be monitored by conventional analytical procedures. Illustratively, aliquots of the reaction mixture can be taken at intervals and examined by infrared spectroscopy, nuclear magnetic resonance, and like methods. When the reaction is determined to be substantially complete, the product can be isolated using conventional techniques. Illustratively, the hydrohalide salt formed by the neutralization of the HX with the basic salt is first removed from the reaction mixture by filtration. The filtrate is distilled to remove the solvent and provide a residue. The latter is then purified, if desired, by distillation (if the product is liquid) or by conventional recrystallization methods if the product be a solid.

Illustrative, but not limiting of the diphenyl ethers of formula (Ia) are 4-isopropenyl-4'-nitrodiphenyl ether, 4-isopropenyl-3-methyl-4'-nitrodiphenyl ether, 4-isopropenyl-3,6-dimethyl-4'-nitrodiphenyl ether, 4-isopropenyl-2,3,5,6-tetramethyl-4'-nitrodiphenyl ether, 4-isopropenyl-2-ethyl-4'-nitrodiphenyl ether, 4-isopropenyl-2-phenyl-4'-nitrodiphenyl ether, 4-isopropenyl-2-benzyl-4'-nitrodiphenyl ether, 4-isopropenyl-2-cyclohexyl-4'-nitrodiphenyl ether, 4-isopropenyl-2'-nitrodiphenyl ether, 4-isopropenyl-3'-nitrodiphenyl ether, 4-isopropenyl-2'-methyl-4'-nitrodiphenyl ether, 4-isopropenyl-2',6'-dimethyl-4'-nitrodiphenyl ether, 4-isopropenyl-4'-methyl-2'-nitrodiphenyl ether, 4-isopropenyl-2'-butyl-4'-nitrodiphenyl ether, 4-isopropenyl-2,2'-dimethyl-4'-nitrodiphenyl ether, 4-isopropenyl,2,3,5,6-tetramethyl-2',3',5',6'-tetramethyl-4'-nitrodiphenyl ether, 4-isopropenyl-2,2',6,6'-tetramethyl-4'-nitrodiphenyl ether, 4-isopropenyl-2,2'-diphenyl-4'-nitrodiphenyl ether, 4-isopropenyl-2,2'-dibenzyl-4'-nitrodiphenyl ether, 4-isopropenyl-2,2'-dicyclohexyl-4'-nitrodiphenyl ether, and the like.

The nitro-isopropenyl diphenyl ethers, as noted above, are useful as starting materials for the preparation of known amino-hydroxyl aromatic ethers used as monomers for the preparation of polyamide-esters as disclosed by Imai et al cited supra. To obtain the monomers, the isopropenyl group is oxidized to hydroxyl using known procedures followed by reduction of the nitro group to form the corresponding amino-hydroxy substituted diphenyl ether.

Notably, they also find utility in the formation of what is believed to be a novel class of nitro-haloisopropyl substituted diphenyl ethers having the formula (Ib) according to the generalized equation. The compounds are obtained in high yields by the addition of a hydrohalic acid HX across the double bond of the isopropenyl group. The method employed in the preparation is that typically disclosed by Fritz et al, J. of Polymer Science 10, 1972, pp. 2365 to 2378. The X has the meaning defined above.

The ether (Ia) is dissolved in an inert organic solvent. The term "inert organic solvent" in the present context means a solvent that does not react with either reactant or otherwise interfere with the process. Typical of the solvents which are employed are aromatic solvents such as benzene, toluene, xylene, nitrobenzene, chlorobenzene, dichlorobenzene, and the like; halogenated solvents such as chloroform, carbon tetrachloride, methylene dichloride, trichloroethane, tetrachloroethylene, and the like.

The hydrohalic acid HX is bubbled through or otherwise added to the solution of (Ia) until the reaction is judged to be complete. Generally speaking, an excess of HX is employed. The preferred hydrohalic acids are hydrogen chloride and hydrogen bromide.

Reaction temperature is not critical except to the extent that if it be too high the HX tends to boil off rather than react. Advantageously, the addition is carried out at a temperature of from about −50° C. to about 50° C., preferably from about −10° C. to about 35° C.

The progress of the reaction is easily monitored by the same analytical methods discussed above for the preparation of the compounds (Ia).

Isolation of the reaction product is easily accomplished by removal of the residual HX using such methods as bubbling an inert gas (i.e. nitrogen) through the solution and then removing solvent by the standard methods of distillation and the like. Alternatively, once the reaction is considered complete, the solution can be immediately distilled, preferably under reduced pressure to remove the dissolved HX and the solvent both at the same time. The residual product can be purified, if desired, by conventional methods, particularly by recrystallization.

Any of the isopropenyl ethers can be converted to the 2-haloisopropyl-nitro diphenyl ethers of formula (Ib). Accordingly, typical but not limiting of the 2-haloisopropyl compounds in accordance with the present invention are those corresponding to the compounds (Ia) illustrated above wherein the isopropenyl group in each compound has been converted to the 2-chloroisopropyl, 2-bromoisopropyl, 2-iodoisopropyl, and 2-fluoroisopropyl group.

Unexpectedly, it has been discovered that the 2-haloisopropyl compounds can be used as intermediates in a facile process for the preparation of a new class of aminohydroxy monomers (III) described below. The key step and surprising feature thereof is an alkylation reaction of a phenol (II) by the 2-haloisopropyl compound (Ib) to form the nitro-p-hydroxyphenylisopropyl substituted diphenyl ether (Ic) in the absence of any catalyst. The latter product is then reduced by known methods to form (III), all in accordance with the generalized reaction scheme set forth in the reaction chart below.

The alkylation process is carried out by heating together the 2-haloisopropyl compound and known phenols in at least equimolar proportions and preferably using at least a molar excess of the phenol reactant. The only limitation on the phenols which can be used is the proviso that the para positions relative to the hydroxyl groups be left free of substituents. Illustrative of the phenols which can be used are phenol, 3-methylphenol, 2-methylphenol, 3-butylphenol, 2,6-dimethylphenol, 2,3,5,6-tetramethylphenol, 3-phenylphenol, 3-benzylphenol, 3-cyclohexylphenol, and the like.

Advantageously, the reaction temperature falls within a range of from about 30° C. to about 200° C., preferably from about 40° C. to about 100° C.

In an optional embodiment of the instant process an inert organic solvent is employed. The term "inert organic solvent" has the same connotation as noted previously. Illustrative of the solvents which can be used are those set forth above for the reaction of the isopropenyl compounds (Ia) with HX. Additionally, the diplar aprotic solvents set forth above for the preparation of the isopropenyl compounds can also be employed.

Although not essential, it is preferred that atmospheric moisture be excluded during the course of the alkylation process using standard procedures, i.e. carrying out the process under an inert atmosphere such as nitrogen, argon, and the like.

The progress of the reaction can be monitored by conventional analytical procedures and methods such as those described hereinbefore. Isolation of the product (Ic) is readily accomplished via conventional means. In the event that a solvent is employed it is removed by known distillation procedures to provide the product as residue. Alternatively, if an excess of the phenol reactant is employed as solvent, then it can be removed by distillation or alternative procedures to provide the product residue. Generally speaking, the nitro p-hydroxyphenylisopropyl substituted diphenyl ethers are solids and can be isolated and/or purified by conventional recrystallization methods.

Illustrative, but not limiting of the hydroxyphenylisopropyl compounds (Ic) in accordance with the present invention are 4-[2-(p-hydroxyphenyl)isopropyl]-4'-nitrodiphenyl ether, 4-[2-(p-hydroxyphenyl)isopropyl]-2'-nitrodiphenyl ether, 4-[2-(p-hydroxyphenyl)isopropyl]-3-methyl-4'-nitrodiphenyl ether, 4-[2-(p-hydroxyphenyl)isopropyl]-2,3,5,6-tetramethyl-4'-nitrodiphenyl ether, 4-[2-(p-hydroxyphenyl)isopropyl]-2-phenyl-4'-nitrodiphenyl ether, 4-[2-(p-hydroxyphenyl)isopropyl]-2-benzyl-4'-nitrodipenyl ether, 4-[2-(p-hydroxyphenyl)isopropyl]-2-cyclohexyl-4'-nitrodiphenyl ether, 4-[2-(p-hydroxyphenyl)isopropyl]-2,2'-diphenyl-4'-nitrodiphenyl ether, 4-[2-(p-hydroxyphenyl)isopropyl]-2,2'-dibenzyl-4'-nitrodiphenyl ether, 4-[2-(p-hydroxyphenyl)isopropyl]-2'-methyl-4'-nitrodiphenyl ether, 4-[2-(p-hydroxyphenyl)isopropyl]-2',6'-dimethyl-4'-nitrodiphenyl ether, 4-[2-(p-hydroxyphenyl)isopropyl]-4'-methyl-2'-nitrodiphenyl ether, 4-[2-(p-hydroxyphenyl)isopropyl]-2'-butyl-4'-nitrodiphenyl ether, 4-[2-(p-hydroxyphenyl)isopropyl]-2,2'-dimethyl-4'-nitrodiphenyl ether, 4-[2-(p-hydroxyphenyl)isopropyl]-2,2',6,6'-tetramethyl-4-nitrodiphenyl ether, 4-[2-(p-hydroxy-2-methylphenyl)isopropyl]-4'-nitrodiphenyl ether, 4-[2-(p-hydroxy-2-methylphenyl)isopropyl]-3,6-dimethyl-4'-nitrodiphenyl ether, 4-[2-(p-hydroxy-2-methylphenyl)isopropyl]-2-phenyl-4'-nitrodiphenyl ether, 4-(2-(p-hydroxy-2-methylphenyl)isopropyl]-2-benzyl-4'-nitrodiphenyl ether, 4-[2-(p-hydroxy-2-ethylphenyl)isopropyl]-2-cyclohexyl-4'-nitrodiphenyl ether, 4-[2-(p-hydroxy-2-ethylphenyl)isopropyl]-2,2'-diphenyl-4'-nitrodiphenyl ether, 4-[2-(p-hydroxy-2-methylphenyl)isopropyl]-2,2'-dibenzyl-4'-nitrodiphenyl ether, 4-[2-(p-hydroxy-2-methylphenyl)isopropyl]-2,2',6,6'-tetramethyl-4'-nitrodiphenyl ether, 4-(2-(p-hydroxy-2-ethylphenyl)isopropyl]-2,6'-dimethyl-4'-nitrodiphenyl ether, 4-[2-(p-hydroxy-2,3,5,6-tetramethylphenyl)isopropyl]-4'-nitrodiphenyl ether, 4-[2-(p-hydroxy-2-phenylphenyl)isopropyl]-4'-nitrodiphenyl ether, 4-[2-(p-hydroxy-2-benzylphenyl)isopropyl]-4'-nitrodiphenyl ether, 4-[2-(p-hydroxy-2-cyclohexylphenyl)isopropyl]-4'-nitrodiphenyl ether, and the like.

The above nitro compounds are easily reduced using conventional hydrogenation methods to form the corresponding amino-p-hydroxyphenylisopropyl substituted diphenyl ethers of formula (III) in accordance with the present invention. For typical methods and detailed teaching in respect of the reduction of aromatic nitro groups to amine groups see Catalytic Hydrogenation over Platinum Metals by Paul N. Rylander, 1967, p. 168 et seq. Academic Press, New York, N.Y. Any of the procedures disclosed therein can be employed in the hydrogenation of (Ic) to (III).

A particularly preferred method comprises the hydrogenation of a solution of (Ic) in a known hydrogenation solvent such as a lower aliphatic alcohol (e.g. methanol, ethanol, propanol, and the like) or aliphatic ester (e.g. ethyl acetate, butyl acetate, and the like) over a palladium on charcoal catalyst. The concentration of (Ic) in the solvent is in no way critical to the course of the reduction. Illustratively, it can be present in a range of from about 5 percent to about 50 percent by weight of the solution.

The palladium can be employed at a convenient concentration on the charcoal support, typically 5 to 25 percent by weight on charcoal.

Hydrogen pressure can fall within any desired range, but, more importantly, within the constraints of the actual hydrogenation apparatus being employed. A convenient apparatus is the well-known Parr Shaker wherein the hydrogen pressure can fall within a range of from about 20 psi to about 80 psi.

Reduction temperature is most conveniently ambient room temperature (i.e. about 20° C.).

Generally speaking, the reduction of the nitro group is completed within a matter of hours under the conditions described above. However, it will be readily understood by one skilled in the art that reaction times will vary depending on the substituents, if any, on the aromatic ring containing the nitro group and on other factors such as actual hydrogen pressure, catalyst activity, and the like.

The amine products are isolated from the reaction mixture using conventional procedures. For example, the catalyst is removed by filtration and the solvent removed by distillation to provide the residual product. Generally speaking, the compounds (III) are crystalline materials, and, if desired, purified by known crystallization procedures.

Any of the nitro compounds can be reduced to the corresponding amino compounds. Accordingly, typical but not limiting of the amino compounds in accordance with the present invention are those corresponding to nitro compounds (Ic) illustrated above wherein the nitro group in each case has been converted to an amino group.

The amino phenols (III) are particularly useful in the preparation of polyamide-esters having recurring units selected from the formulae (IV), (V), and mixtures thereof as illustrated in the formula chart.

The polyamide-esters in accordance with the present invention are prepared by reacting in substantially equimolar proportions the amino-phenol (III) with a diacid halide having the formula (VIII) wherein X and D are defined above.

Because of differences in reactivity from one monomer reactant to another in addition to reactivity differences between the reaction of a phenol with acid halide to form ester versus an amine with acid halide to form amide, the recurring units in the polymers can have the formulae (IV), (V), or predominantly a randomized mixture thereof.

Illustrative of the diacid halides are glutaroyl dichloride, glutaroyl dibromide, adipoyl dichloride, pimeloyl dichloride, suberoyl dichloride, azelaoyl dichloride, sebacoyl dichloride, isophthaloyl dichloride, isophthaloyl dibromide, terephthaloyl dichloride, terephthaloyl dibromide, cyclohexane-1,4-dicarboxylic acid dichloride, and the like.

The polymers can be prepared using any of the procedures disclosed in the art for polymerizing aminophenols with diacid halides. Accordingly, they can be prepared by interfacial polymerization, two-phase polymerization with a phase transfer catalyst, solution polymerization, and even melt polymerization methods, although the latter method is least preferred. For a detailed teaching in respect of the first three methods see Imai et al cited supra. For a melt polymerization procedure see C. Giori Polymer Preprints American Chemical Society, Division of Polymer Chemistry 12, 606 (1971).

Preferably, the polyamide-esters are prepared by the interfacial polymerization method wherein the aminophenol along with at least a 2 molar excess of a strong base (i.e. sodium hydroxide, potassium hydroxide, and the like) are first dissolved in water. The aqueous solution is then stirred very rapidly and the temperature maintained at least as low as ambient room temperature (about 20° C.) for the next step in the process.

The acid halide is added to the rapidly stirred aqueous solution as a solution in a water immiscible organic solvent. Typical of such solvents are the halogenated solvents such as methylene dichloride, trichloroethane, cyclohexanone, and the like. Polymer formation is almost immediate and the mixture can be stirred for an additional time period, if desired, to ensure maximum polymer formation.

Isolation of the polymer is readily accomplished by conventional filtration techniques and purification steps can include washing the isolated polymer with hot water to remove traces of salt. Optionally, additional purification steps to remove low molecular weight polymer can be carried out by heating the polymer with solvents such as ethyl acetate, dibutyl ether, and the like.

The polyamide-esters are thermoplastic and characterized by good melt processability such as extrudability, injection moldability, and the like, and are capable of film, and fiber formation. Generally speaking, the polymers are soluble in cresol as well as dipolar aprotic solvents.

The polymers are further characterized by an inherent viscosity value of at least 0.5 as determined for a 0.5 percent by weight solution in N-methylpyrrolidone at about 30° C.

Particular polymer properties will vary according to such factors as whether the radical D is arylene, alkylene, or cycloalkylene, whether para-para, or para-ortho isomers are used, and the extent to which the aromatic rings of the amino-phenol (III) are substituted. Needless to say, the greater the aromaticity and linearity of the polymer, the higher its fusion range.

While any of the polyamide-ester polymers of the invention possess useful and advantageous properties, preferred is that class of polymers having all para-para linkages in the polymer chain wherein the amide nitrogen linkages in said recurring units (IV) and (V) are in the para position relative to the ether linkage in the same aromatic ring. Most preferred within this class are those polymers wherein R, $R^1$, and $R^2$ are each alkyl; n, m, and p each have an independent value of 0 to 2, inclusive, and D represents arylene.

Accordingly, and to the extent that polyamide-esters of the invention are the desired products, the preferred and most preferred classes in the preceding chain of compounds of the invention having the formulae (I) and (III) are such that their limitations will give rise to the preferred and most preferred classes of polyamide-esters described above.

The polyamide-esters of the invention have melt temperatures which are ideally suited for injection molding or compression molding to produce articles such as bushings, seal faces, compressor vanes, and impellers, gaskets, wire coating, bellows tubing, hose (particularly bellows hosing for engines), and the like.

The following examples describe the manner and process of making and using the invention and set forth the best mode contemplated by the inventor of carrying out the invention but are not to be construed as limiting.

EXAMPLE 1

Preparation of p-Isopropenylphenol

A distillation flask equipped with a Vigreux column was charged with 70.0 g. (0.31 mole) of bisphenol A

[2,2-bis(p-hydroxyphenyl)propane] and 0.2 g. of sodium hydroxide. The bisphenol A was pyrolyzed under reduced pressure at a bath temperature of 200° to 270° C. Over a period of about 50 minutes and under 10 mm. of pressure (mercury) a distillate of 68.1 g. of a mixture of phenol and isopropenylphenol was obtained.

The mixture was distilled to remove the phenol, b.p.=88° to 95° C. (10 mm. of mercury pressure), wt.=27.4 g. and leave a residue of a mixture of isopropenylphenol and isopropenylphenol dimers. The latter was cracked using the same type of distillation procedure as above under 10 mm. of mercury pressure and a bath temperature of about 220° to 280° C. and there was collected 39.1 g. (0.29 mole) (94% yield) of p-isopropenylphenol, b.p.=125° to 150° C. The isopropenylphenol was dissolved in 200 ml. of dimethylacetamide and employed as a stock solution in preparations described below.

The following experiment describes the preparation of 4-isopropenyl-4'-nitrodipenyl ether in accordance with the present invention.

A 500 ml. reaction flask equipped with a stirrer, thermometer, reflux condenser, and addition funnel was charged with 25 g. (0.16 mole) of p-chloronitrobenzene dissolved in 100 ml. of dimethylacetamide along with 21 g. of sodium carbonate (0.2 mole), and 0.1 g. of p-methoxyphenol as an inhibitor to prevent the polymerization of isopropenylphenol.

The contents of the flask were heated to about 150° to 160° C. and during stirring 100 ml. of the dimethylacetamide solution of isopropenylphenol obtained above (19.6 g. or 0.15 mole) was added over a 2.5 hour period followed by an additional 10 hour stirring at 150° to 160° C. The mixture was cooled to ambient temperature (about 20° C.) and the precipitate sodium chloride was separated by suction filtration. The salt cake was washed with a small amount of ethyl acetate. Solvent was removed under reduced pressure to yield a residue which was then vacuum distilled. The main distillate had a b.p.=150° to 160° C. (0.1 mm. of mercury pressure) and solidified to a crystalline solid; wt.=32.7 g. (m.p. not determined). Repetition of the reaction using essentially the same procedure provided 36.9 g. of crystalline solid; m.p. 45° to 48° C. Proton nuclear magnetic resonance (NMR) showed both products to be identical and consistent with the expected structure. Thus there was obtained a total yield of 90.7 percent of 4-isopropenyl-4'-nitrodiphenyl ether in accordance with the present invention. The product was recrystallized from ethanol, melted at 50° to 51° C., and had the following elemental analysis.

Calcd. for $C_{15}H_{13}NO_3$: C, 70.58%; H, 5.13%; N, 5.49%. Found: C, 70.58%; H, 5.18%; N, 5.50%.

EXAMPLE 2

A reaction flask was charged with 16.0 g. (0.063 mole) of 4-isopropenyl-4'-nitrodiphenyl ether prepared in Example 1. The ether was dissolved in 80 ml. of methylene dichloride and during stirring dry hydrogen chloride gas was bubbled into the solution at ambient temperature (about 20° C.).

After 1.5 hours of passing the hydrogen chloride through the solution an NMR analysis of an aliquot sample showed the absence of any vinyl protons. The solvent was removed using a rotary evaporator under aspirator pressure (about 10 mm. of mercury pressure) and using a temperature no greater than 60° C. A solid residue formed which was recrystallized from 20 ml. of a 1:1 (by volume) mixture of hexane:cyclohexane.

Thus there was obtained 13.6 g. (75 percent yield) of 4-(2-chloroisopropyl)-4'-nitrodiphenyl ether in accordance with the present invention; m.p. 58° to 61° C. The compound had the following analysis.

Calcd. for $C_{15}H_{14}NO_3Cl$: C, 61.76%; H, 4.84%; N, 4.80%. Found: C, 62.80%; H, 5.04%; N, 4.89%.

The product was completely stable under ambient temperature conditions (about 20° C.). However, when heated above 80° C. it evolved hydrogen chloride gas.

EXAMPLE 3

A round bottom flask was charged with 12.0 g. (0.05 mole) of 4-isopropenyl-4'-nitrodiphenyl ether dissolved in 50 ml. of methylene dichloride. The solution was treated according to the procedure described in Example 2 above by passing in dry hydrogen chloride gas until NMR analysis showed the lack of vinyl protons. Removal of solvent provided 14.6 g. (about 100 percent crude yield) of the 4-(2-chloroisopropyl-4'-nitrodiphenyl ether.

In a separate flask, 18.8 g. (0.2 mole) of phenol was heated to about 80° C. with stirring. Under a nitrogen atmosphere and over a 15 minute period, the solid 4-(2-chloroisopropyl)-4'-nitrodiphenyl ether was added in portions. The reaction mixture exothermed and hydrogen chloride was evolved. After completion of the addition, the phenol solution was stirred for an additional 45 minute period (total time of 1 hour).

The excess phenol was removed by distillation under vacuum (b.p.=60° to 65° C. under 0.2 mm. of mercury pressure) leaving a residual oil. The oil was diluted with 75 ml. of toluene and cooled to 5° C. resulting in the formation of a crystalline precipitate. It was collected by suction filtration and dried. Thus, there was obtained 13.9 g. (85% yield from the starting isopropenyl derivative) of 4-[2-(p-hydroxyphenyl)isopropyl]-4'-nitrodiphenyl ether in accordance with the present invention; m.p. 118° to 120° C. The same compound, but obtained from a different preparation in accordance with this same Example, had the following elemental analysis.

Calcd. for $C_{21}H_{19}NO_4$: C, 72.19%; H, 5.48%; N, 4.01%. Found: C, 72.15%, H, 5.52%; N, 3.94%.

EXAMPLE 4

A 17 g. (0.05 mole) sample of the 4-[2-(p-hydroxyphenyl)isopropyl]-4'-nitrodiphenyl ether was hydrogenated at room temperature (about 20° C.) in a 500 ml. pyrex pressure flask using a Parr hydrogenation apparatus. The solvent employed was 100 ml. of ethanol and the catalyst was 0.2 g. of 10% palladium on charcoal. The hydrogen pressure was about 50 psi and after about 20 hours the total hydrogen uptake was 12 psi or ~0.17 mole.

The reaction solution was worked up by first filtering off the catalyst followed by stripping off the ethanol using a rotary evaporator under reduced pressure. A solid residue was obtained which was recrystallized from 50 ml. of hot toluene. Thus, there was obtained 14.9 g. (93 percent yield) of 4-[2-(p-hydroxyphenyl)isopropyl]-4'-aminodiphenyl ether in accordance with the present invention; m.p. 150° to 152° C. The same compound but obtained from a different preparation in accordance with this Example had the following elemental analysis.

Calcd. for $C_{21}H_{21}NO_2$: C, 78.97%; H, 6.63%; N, 4.39%. Found: C, 78.74%; H, 6.67%; N, 4.12%.

EXAMPLE 5

A 3 liter Morton flask was equipped with a high speed stirrer, addition funnel, thermometer, and vent tube. A potassium hydroxide solution was prepared by dissolving 1.30 g. (0.020 mole) of 87 percent pure material in 1000 ml. of distilled water in the flask. A 3.194 g. (0.01 mole) sample of 4-[2-(p-hydroxyphenyl)isopropyl]-4'-aminodiphenyl ether was dissolved in 200 ml. of methylene dichloride and added to the potassium hydroxide solution at ambient temperature (about 20° C.). The addition funnel was charged with a solution consisting of 2.04 g. (0.01 mole) of pure terephthaloyl chloride dissolved in 500 ml. of methylene dichloride. The contents of the flask were rapidly stirred (500 rpm) and while being cooled to maintain the temperature at the ambient level (about 20° C.) the contents of the addition funnel were added over a 5 minute period. A white precipitate formed almost immediately and the reaction mixture was rapidly stirred for about 30 minutes.

The precipitate was collected by suction filtration and thoroughly washed with hot water. After oven drying, the white polymer product weighed 4.03 g. Further purification to remove low molecular weight material was effected by adding the polymer to 200 ml. of ethyl acetate and stirring for 30 minutes at 80° C. The insoluble polymer was filtered while the mixture was still hot. It was dried in a vacuum oven (about 0.1 mm. of mercury) at 80° C. overnight.

Thus there was produced 2.85 g. (63 percent yield) of a polyamide-ester in accordance with the present invention having a mixture of the following recurring units

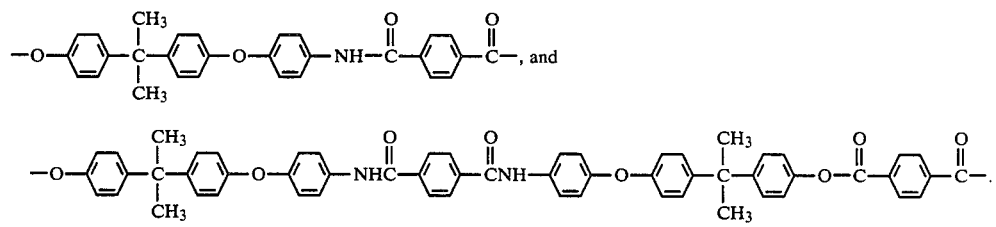

The polymer had an $\eta_{inh}$ at 30° C. (0.5% in N-methylpyrrolidone)=0.81; fusion temperature range of 275° C. to 320° C.

FORMULA CHART

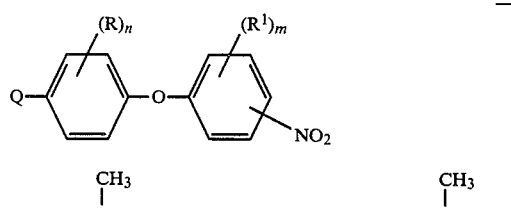

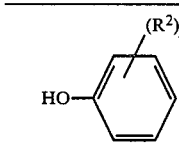

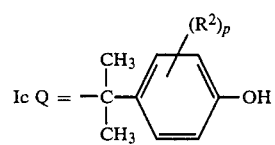

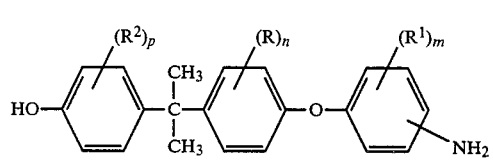

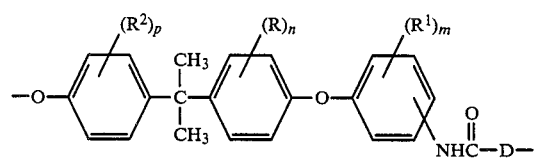

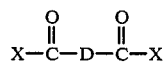

REACTION CHART

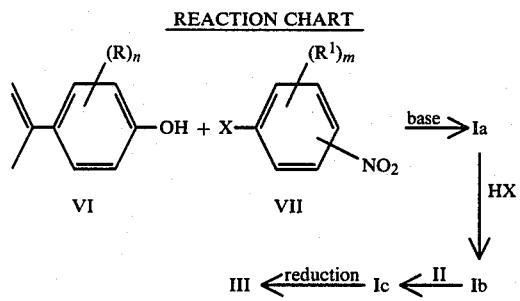

I claim:
1. A nitro substituted diphenyl ether having the formula

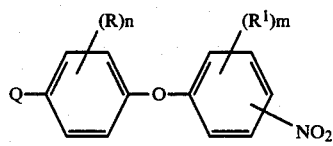

wherein
Q is

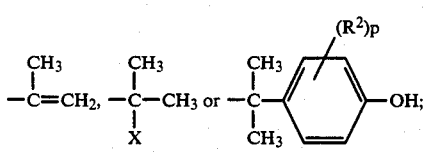

R, $R^1$, and $R^2$ are independently selected from the group consisting of alkyl, aryl, aralkyl, and cycloalkyl;
X represents halogen; and n, m, and p each have an independent value of 0 to 4, inclusive.

2. A diphenyl ether according to claim 1 wherein the nitro group is in the para position relative to the ether linkage.

3. A diphenyl ether according to claim 1 wherein Q is

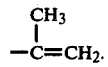

4. A diphenyl ether according to claim 3 wherein R and $R^1$ are each alkyl, n and m each have an independent value of 0 to 2, inclusive and the nitro group is in the para position relative to the ether linkage.

5. A diphenyl ether according to claim 4 wherein n and m are zero.

6. A diphenyl ether according to claim 1 wherein Q is

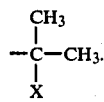

7. A diphenyl ether according to claim 6 wherein X is chlorine.

8. A diphenyl ether according to claim 7 wherein R and $R^1$ are each alkyl, n and m each have an independent value of 0 to 2, inclusive and the nitro group is in the para position relative to the ether linkage.

9. A diphenyl ether according to claim 8 wherein n and m are zero.

10. A diphenyl ether according to claim 1 wherein Q is

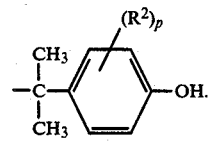

11. A diphenyl ether according to claim 10 wherein R, $R^1$ and $R^2$ are each alkyl, n, m and p each have an independent value of 0 to 2, inclusive, and the nitro group is in the para position relative to the ether linkage.

12. A diphenyl ether according to claim 11 wherein n, m and p are zero.

* * * * *